United States Patent [19]

Narukawa et al.

[11] 4,425,356

[45] Jan. 10, 1984

[54] LANKACIDIN DERIVATIVES USED IN SWINE HUSBANDRY

[75] Inventors: Noriaki Narukawa; Keinosuke Takeda, both of Fukuchiyama; Toshiyuki Yamazaki, Kawanishi, all of Japan

[73] Assignee: Takeda Chemical Industries, Ltd., Osaka, Japan

[21] Appl. No.: 324,635

[22] Filed: Nov. 24, 1981

[30] Foreign Application Priority Data

Nov. 29, 1980 [JP] Japan .............................. 55-168979
Jul. 3, 1981 [JP] Japan .............................. 56-104583

[51] Int. Cl.$^3$ .................. A61K 31/365; C07D 309/30
[52] U.S. Cl. ........................................... 424/279; 424/266; 546/256; 546/269; 549/269; 549/270
[58] Field of Search ............... 424/279, 266; 549/269, 549/270; 546/256, 269

[56] References Cited

U.S. PATENT DOCUMENTS

| | | | |
|---|---|---|---|
| 3,118,812 | 1/1964 | Gäumann et al. | 435/128 |
| 3,626,055 | 12/1971 | Higashide et al. | 424/121 |
| 3,676,300 | 7/1972 | Yamamoto et al. | 549/270 |
| 3,691,181 | 9/1972 | Kishi et al. | 424/283 |
| 4,205,081 | 5/1980 | Sakamoto et al. | 424/279 |

OTHER PUBLICATIONS

Harada et al., (I) The Jour. of Antibiotics, vol. 26, pp. 647–657 (1973).
Harada et al., (II) Chem. Pharm. Bull. 22(1), 99–108, 1974.
Harada et al., (IV) CA 68028p, vol. 82, 1975.
Harada et al., (IV) CA 84:173591f.
E. Higashide et al., Journal of Antibiotics, 24, No. 1 (1971) pp. 1–12.
S. Harada et al., Journal of Antibiotics, 24, No. 1 (1971) pp. 13–22.
T. Fugono et al., Journal of Antibiotics, 24, No. 1 (1971) pp. 23–28.
K. Tsuchiya et al., Journal of Antibiotics, 24, No. 1 (1971), pp. 29–41.
K. Ootsu et al., (I), Gann, 64, pp. 481–495, (1973).
K. Ootsu et al., (II), Cancer Chemotherapy Report Part 1, vol. 59, No. 5, pp. 919–928 (1975).
Derwent Basic No. 11894, The English Translation of Japanese Patent Publication 4848/64.
J. M. J. Sakamoto et al., Journal of Antibiotics SER. A, vol. No. 2, pp. 98–102, (1962).
M. Uramoto et al., Tetrahedron Letters, No. 27, pp. 2249–2254, (1969).
M. Uramoto et al., Agr. Biol. Chem., vol. 35, No. 1, pp. 27–32, (1971).
B. J. Williams et al., Veterinary Medicine/Small Animal Clinician vol. 73, pp. 349–351, (1978).

Primary Examiner—Jane T. Fan
Attorney, Agent, or Firm—Wenderoth, Lind & Ponack

[57] ABSTRACT

Compound of the formula:

wherein $R^1$ is =O or $$<^H_{OH,}$$

and $R^2$ and $R^3$ are each hydrogen or carboxylic acid-derived acyl, are effective for prophylaxis or treatment of swine dysentery or for increase of swine productivity.

10 Claims, No Drawings

LANKACIDIN DERIVATIVES USED IN SWINE HUSBANDRY

The present invention relates to an improvement in swine husbandry.

More particularly, this invention provides a method for prophylaxis and treatment of swine dysentery or for increase of swine productivity, which comprises administering to swine one or more compounds of the formula:

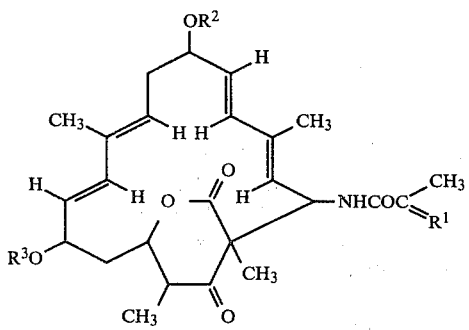

wherein $R^1$ is $=O$ or

and $R^2$ and $R^3$ are each hydrogen or carboxylic acid-derived acyl, and another object is to provide a composition for prophylaxis and treatment of swine dysentery or for increase of swine productivity containing compound (I). Other objects will be made clear from the description and claims presented hereinafter.

Swine dysentery is an epidemic intestinal disease in swine, as caused by *Treponema hyodysenteriae* a dominant symptom of which is bloody mucous diarrhea. The high incidence of this disease has been observed in most of the countries where swine are raised. Once there is an outbreak, the disease becomes ubiquitous in the area and is extremely difficult to eradicate, causing, wherever large herds are kept, so much reduced feed efficiencies, which contributes to serious economic losses.

Various drugs have heretofore been employed for the prophylaxis and treatment of swine dysentery but none has proved fully satisfactory because some of them are not sufficiently effective while others are accompanied by serious untoward effects or are suspicious of safety, especially of carcinogenesis.

With such prior art in the background, the present inventors, as a result of intensive investigation, unexpectedly have found that compound (I) displays a marked prophylactic and therapeutic action on swine dysentery, which has never been obtained with the drugs hitherto used, and furthermore have found that compound (I) promotes growth of swine and improves feed efficiency, thereby increases productivity in swine raising. The compound (I) can be used in safety in swine husbandry, therefore is very useful in the livestock industry.

Compound (I) includes antibiotic substances, which form the T-2636 antibiotics group, isolated from the culture of *Streptomyces rochei* var. volubilis and collectively called lankacidins, and derivatives thereof. As for lankacidin A ($R^1$: $=O$, $R^2$: H, $R^3$: COCH$_3$), lankacidin C ($R^1$: $=O$, $R^2$: H, $R^3$: H), lankacidinol A ($R^1$:

$R^2$: H, $R^3$: COCH$_3$) and lankacidinol ($R^1$:

$R^2$: H, $R^3$: H), among others, the organism capable of producing these, methods of production thereof and physicochemical and biological properties thereof are described in the Journal of Antibiotics, 24, 1-41 (1971), for instance; as for lankacidin A 8-propionate ($R^1$: $=O$, $R^2$: COCH$_2$CH$_3$, $R^3$: COCH$_3$), lankacidin C 8-acetate ($R^1$: $=O$, $R^2$: COCH$_3$, $R^3$: H), lankacidin C 8-propionate ($R^1$: $=O$, $R^2$: COCH$_2$CH$_3$, $R^3$: H), lankacidin C 14-propionate ($R^1$: $=O$, $R^2$: $R^2$: H, $R^3$: COCH$_2$CH$_3$), lankacidin C 8,14-diacetate ($R^1$: $=O$, $R^2$, $R^3$: COCH$_3$), lankacidin C 8,14-dipropionate ($R^1$: $=O$, $R^2$, $R^3$: COCH$_2$CH$_3$) lankacidin C 8-benzoate ($R^1$: $=O$, $R^2$: COPh, $R^3$: H), lankacidin C 14-benzoate ($R^1$: $=O$, $R^2$: H, $R^3$: COPh), lankacidin C 14-phenylpropionate ($R^1$: $=O$, $R^2$: H, $R^3$: COCH$_2$CH$_2$Ph) and lankacidin C 14-nicotinate ($R^1$: $=O$, $R^2$: H, $R^3$: nicotinoyl), among others, the methods of production thereof and their physicochemical and biological properties are disclosed in the Journal of Antibiotics, 26, 647-657 (1973), for instance; and as for lankacidin C 14-formate ($R^1$: $=O$, $R^2$: H, $R^3$: COH), the method of production thereof and physicochemical properties are disclosed in U.S. Pat. 3,676,300, for instance.

The organism, *Streptomyces rochei* var. volubilis, which is capable of producing lankacidin A, lankacidin C, lankacidinol A and lankacidinol, is deposited at the Institute for Fermentation, Osaka and the American Type Culture Collection under accession numbers IFO 12507 and ATCC 21250, respectively.

The carboxylic acid-derived acyl group represented by $R^2$ and $R^3$ in the above general formula (I) is preferably a lower fatty acid residue (especially containing 1-7 carbon atoms, e.g. formyl, acetyl, propionyl, butyryl, isobutyryl, valeryl, hexanoyl) or an aromatic carboxylic acid residue (e.g. aryl carboxylic acid residue such as benzoyl, heteroaromatic carboxylic acid residue such as nicotinoyl). Said lower fatty acid residue may be substituted with phenyl group on the terminal carbon atom thereof (e.g. phenylacetyl, phenylpropionyl, etc.).

Especially preferred examples of compound (I) usable in accordance with the invention are those compounds wherein $R^2$ and $R^3$ are each hydrogen or C$_{2-4}$ fatty acid residue. Among others, lankacidin A, lankacidin C, lankacidin C 14-propionate, lankacidin C 8-acetate, lankacidin C 8-propionate, lankacidinol A, lankacidinol, and mixtures of these are preferably used. The use of lankacidin A and/or lankacidin C is especially advantageous.

The composition for swine use according to the invention may contain one species of compounds (I) or may contain simultaneously two or more species of compounds (I), for example, a mixture of a predominant amount of lankacidin A with lankacidin C. In addition, fermentation media obtained by cultivating the above-mentioned organism *Streptomyces rochei* var. volubilis, may also be used as dried products or extracts thereof.

The composition for preventing or treating swine dysentery, or for increasing swine productivity according to this invention may be prepared by formulating compound (I) into such dosage forms as powders, granules, tablets, liquid, paste, capsules, injectable, solution, etc. either together with a solid or liquid diluent, without a diluent or after stabilization by coating, or by adding compound (I) to feed or drinking water either directly or after having been dispersed into a diluent to prepare a premix. The diluent includes usual carrier, vehicle and diluent.

The diluent may be any which is per se physiologically acceptable, and is desirably the one which can serve as a feed or a component thereof. Generally, compound (I) is formulated into feed, or once formulated into premix and the premix is incorporated into feed to be served. The solid diluents are, for example, basal feedstuffs for swine such as barley flour, wheat flour, rye flour, corn meal, soybean flour, soybean meal, rapeseed meal, chaff, rice bran, defatted rice bran, sweet potato powder, white potato powder, soybean curd cake, starch, lactose, sucrose, glucose, fructose, yeast, waste yeast, fish metal and so on; and inorganic materials e.g. talcum, white clay, clay. The liquid diluent is, for example, water, physiological saline or a physiologically acceptable organic solvent.

Suitable auxiliaries, such as an emulsifying agent, dispersing agent, suspending agent, wetting agent, thickening agent, gelling agent, solubilizing agent and stabilizing agent, may be added in adequate amounts. Furthermore, an antiseptic, fungicide, antibiotic, yeast preparation and/or lactobacillus preparation may be formulated. The composition may also contain vitamins, minerals and amino acids. As the minerals, for example, manganese (e.g., manganese carbonate, manganese sulfate), iron (e.g., ferrousfumarate, ferrous sulfate), cobalt (e.g., cobaltous sulfate, cobaltous chloride), copper (e.g., cupric sulfate, cupric phosphate, cupric chloride), zinc (e.g., zinc carbonate, zinc chloride), iodine (e.g., calcium iodate, calcium iodide, sodium iodide) can be mentioned. Vitamins include water-insoluble (e.g., vitamin A, vitamin $D_3$) and water-soluble vitamins (e.g., vitamin $B_1$, vitamin C), and amino acids include essential amino acids (e.g., D,L-methionine, lysine).

The composition of this invention in a form of feed advantageously contains, as diluent, corn meal and/or soybean meal and in a form of premix advantageously further contains one or more minerals which should be contained in a feed to be served.

The compound (I) of the present invention can be advantageously once formulation into premix and administered to swine as an admixture of the premix with diluents. Such a premix can advantageously contains compound (I) at a weight concentration of about 0.5 to 80%, preferably about 1 to 50%.

The composition containing compound (I) of this invention can be produced, for example, by admixing compound (I) and the above-mentioned diluents. Regarding the premix of this invention, it can be produced by admixing further with one or more minerals.

The composition preferably can be formulated into a solid in view of the practical use, i.e. for stabilizing the compound (I), distribution and serving.

The proper dosage of the compound (I) of the invention for prophylaxis or treatment of swine dysentery or for increase of swine productivity may be suitably selected depending upon the age and conditions of swine, route of administration, etc.

Generally, compound (I) is orally administered to swine in an amount of about 0.025 to 25 mg per kilogram body weight, and practically a feed containing compound (I) in a weight concentration of about 0.5 to 500 ppm is orally administered ad libitum to swine.

More particularly, for the prophylaxis of swine dysentery, it is preferable to administer compound (I) at the dose level of about 0.05 to 25 mg/kg/day, suitably by incorporating compound (I) to a feed in a concentration of about 1 to 500 ppm, preferably 2 to 200 ppm. In treating swine dysentery, it is preferable to administer compound (I) at the dose level of about 1 to 25 mg/kg/day, suitably by incorporating compound (I) to a feed in a concentration of about 2 to 500 ppm, preferably about 2.5 to 200 ppm. On the other hand, for the purpose of increasing swine productivity it is preferable to administer about 0.025 to 10 mg/kg/day of compound (I), suitably by incorporating the same to a feed in a concentration of about 0.5 to 200 ppm, preferably about 1 to 100 ppm.

The toxicity of compound (I) in animals is very low. For example, in acute toxicity tests with mice, the oral $LD_{50}$ value was more than 10,000 mg/kg for each of lankacidin C, lankacidin C 14-propionate and lankacidin A, and the intraperitoneal $LD_{50}$ value was 8,000–10,000 mg/kg for lankacidin A, more than 10,000 mg/kg for lankacidin C 14-propionate and 4,500 mg/kg for lankacidin C.

This fact not only indicates high safety to human being in production and distribution but also means a greater tolerance of the animal medicate. Thus, when compound (I) is administered as incorporated in feed, even a fair degree of unhomogeneity in the admixing stage does not effect appreciably on the safety of the agent to subject animals.

The following test examples and dosage form examples will illustrate the invention in further detail, but are by no means limitative of the invention.

TEST EXAMPLE 1

Several agents were tested for in vitro antibacterial activity against *Treponema hyodysenteriae*, the pathogenic bacteria causing swine dysentery, by the method of testing drug sensitivity of *Treponema hyodysenteriae* (Kashiwazaki et al. Abstracts of Papers presented at the 82nd Meeting of the Japanese Society of Veterinary Science, page 101, 1976). The results obtained are shown in Table 1. Lankacidin C exhibited strong antibacterial activity, whereas other antibiotics used for comparison were all ineffective.

TABLE 1

| Agent | Minimum Inhibitory Concentration (μg/ml) Strain | | | |
|---|---|---|---|---|
| | CD1 | DJ70P1 | MK-2 | 78/A |
| Lankacidin C | 3.13 | 3.13 | 3.13 | 3.13 |
| Erythromycin | >100 | >100 | >100 | >100 |
| Spiramycin | >100 | >100 | >100 | >100 |
| Oleandomycin | >100 | >100 | >100 | >100 |
| Leucomycin | >100 | >100 | >100 | >100 |
| Maridomycin | >100 | >100 | >100 | >100 |

TABLE 1-continued

| | Minimum Inhibitory Concentration (μg/ml) Strain | | | |
|---|---|---|---|---|
| Agent | CD1 | DJ70P1 | MK-2 | 78/A |
| Lincomycin | 50 | 50 | 50 | 50 |

(1) Strains: These strains belong to *Treponema hyodysenteriae* isolated from the bloody mucous faeces of dysenteric pigs in Japan.
(2) Antimicrobial activity assay: Agar dilution method
(3) Inoculum size: A loopful of bacterial suspension ($10^6$ CFU/ml)
(4) Cultural conditions: GasPak anaerobic system (BBL), 37° C., 2 days

TEST EXAMPLE 2

Typical agents among compound (I) were tested for in vitro antibacterial activity by the same method as in Test Example 1. The results are shown in Table 2. These agents exhibited strong antibacterial activity against *Treponema hyodysenteriae* though there appeared some difference at their MIC values from one another.

TABLE 2

| | Minimum Inhibitory Concentration (μg/ml) Strain | | | |
|---|---|---|---|---|
| Compound (I) | DJ70P1 | MK-2 | 78/A | CD-1 |
| Lankacidin A | 6.25 | 3.13 | 3.13 | 6.25 |
| Lankacidin C | 3.13 | 1.56 | 1.56 | 1.56 |
| Lankacidinol A | 25 | 25 | 12.5 | 25 |
| Lankacidinol | 25 | 25 | 12.5 | 12.5 |
| Lankacidin C 8-acetate | 0.78 | 0.39 | 0.39 | 0.39 |
| Lankacidin C 8-propionate | 1.56 | 1.56 | 1.56 | 1.56 |
| Lankacidin C 14-propionate | 3.13 | 1.56 | 1.56 | 3.13 |

Notes:
The experimental conditions are the same as in Test Example 1 (Table 1).

TEST EXAMPLE 3

Agents of compound (I) were tested for in vitro antibacterial activity by the same method as in Test Example 1. The results are shown in Table 3. All agents exhibited strong antibacterial activity against *Treponema hyodysentenae*.

TABLE 3

| | Minimum Inhibitory Concentration (μg/ml) Strain | | | |
|---|---|---|---|---|
| Compound (I) | DJ70P1 | MK-2 | 78/A | CD-1 |
| Lankacidin A | 3.13 | 6.25 | 3.13 | 6.25 |
| Lankacidin C 8-butyrate | 0.78 | 0.78 | 0.78 | 0.78 |
| Lankacidin C 8-isobutyrate | 3.13 | 6.25 | 6.25 | 6.25 |
| Lankacidin C 8-valerate | 1.56 | 3.13 | 1.56 | 3.13 |
| Lankacidin C 8-benzoate | 0.1 | 0.1 | 0.1 | 0.1 |
| Lankacidin C 14-butyrate | 1.56 | 3.13 | 0.78 | 1.56 |
| Lankacidin C 14-isobutyrate | 12.5 | 25 | 12.5 | 25 |
| Lankacidin C 14-valerate | 3.13 | 6.25 | 3.13 | 6.25 |
| Lankacidin C 14-benzoate | 6.25 | 6.25 | 6.25 | 6.25 |
| Lankacidin C 14-formate | 6.25 | 6.25 | 6.25 | 12.5 |
| Lankacidin C 8,14-diacetate | 3.13 | 1.56 | 3.13 | 3.13 |
| Lankacidin C 8,14-dipropionate | 0.78 | 0.78 | 0.78 | 1.56 |
| Lankacidin C 8,14-dibutyrate | 3.13 | 3.13 | 1.56 | 3.13 |
| Lankacidin A 8-propionate | 6.25 | 6.25 | 6.25 | 6.25 |

TEST EXAMPLE 4

Lankacidin A, lankacidin C, lankacidin C 8-acetate, lankacidin C 14-propionate, lankacidinol A and lankacidinol were tested for efficacy against swine dysentery in experimental infection in mice with swine dysentery.

The similar experimental infection model of swine dysentery in mice as that described, for example, by Joens et al. in Infection and Immunity, 25, 757-760 (1979), American Journal of Veterinary Research, 41, 1225-1226 (1980) and Veterinary Record, 107, 527-529 (1980) was used. Thus, a field isolate of *Treponema hyodysenteriae* anaerobically cultivated on the 5% defibrinated horse blood added Trypticase soy agar (BBL) plate was mashed together with the culture medium and diluted two-fold with Trypticase soy broth (BBL). Mice were inoculated intragastrically with this infecting dilution. Each test agent was suspended in 5% gum arabic solution and forcibly administered orally from day 1 to day 4 following infection. Seven days after infection, the cecum was examined for lesions, and the cecum was mashed together with the contents and subjected to *Treponema hyodysenteriae* counting. The results obtained are summarized in Table 4. Excellent efficacy was produced in each of the drug-administered groups.

TABLE 4

| Agent | Dose (mg/kg/day) | Number of mice from which the pathogen was detected/number of mice tested | Number of mice with cecal lesions/number of mice tested |
|---|---|---|---|
| Infected control | — | 5/5 | 3/5 |
| Lankacidin A | 5 | 1/5 | 0/5 |
| Lankacidin C | 5 | 1/5 | 0/5 |
| Lankacidin C 8-acetate | 5 | 0/5 | 0/5 |
| Lankacidin C 14-propionate | 5 | 1/5 | 0/5 |
| Lankacidinol A | 5 | 1/5 | 0/5 |
| Lankacidinol | 5 | 0/5 | 0/5 |

TEST EXAMPLE 5

Lankacidin C was tested for efficacy against swine dysentery under experimental infection conditions. Thus, twelve 6-week-old Landrace pigs (4 per group) were used. The test drug was admixed to a concentration of 100 ppm with the domestically formulated starter feed for young pigs without antibiotics. The animals were provided with the ration ad libitum. Infection of the pigs was effected by direct intragastrical administration to the SPF pigs of an inoculum prepared by preliminary anaerobic cultivation of the *Treponema hyodysenteriae* 78/A strain on a 5% horse blood added agar plate, mashing together with the culture medium and admixing with 5% mucin added phosphate buffer. Colonic contents and mucosa were collected from pigs which developed typical signs of swine dysentery, and diluted two-fold with 5% mucin added phosphate buffer. The dilution was used as the final inoculum, and 100 ml of the dilution was directly injected into the stomach of test pigs at the age of 7 weeks (fasted for 24 hours before infection). The pigs were fed for 21 days following infection. The results obtained are summarized in Table 5. Whereas maridomycin was ineffective, lankacidin C produced an excellent effect against swine dysentery.

TABLE 5

| Item examined | Group | | |
|---|---|---|---|
| | Infected control | Lankacidin C 100 ppm | Maridomycin 100 ppm |
| Swine dysentery | | | |
| Number of pigs showing signs of infection/number of pigs used | 4/4 | 0/4 | 3/4 |
| Number of days on which mucous bloody stool was observed (during the 21-day test period) | 8.5 | 0 | 5.5 |
| Number of days on which diarrhea was observed (during the 21-day test period) | 14.8 | 0 | 11.0 |
| Number of pigs from which the pathogen was detected | | | |
| In feces | 4 | 0 | 4 |
| In colonic mucosa | 4 | 0 | 4 |
| Number of pigs showing colonic lesions | 4 | 0 | 4 |
| Feeding results | | | |
| Body weight (kg) | | | |
| At the time of infection | 12.5 | 13.6 | 12.8 |
| At the time of completion of test | 17.8$^a$ | 28.5$^b$ | 21.9$^{ab}$ |
| Body weight gain (grams/day) | 251$^a$ | 708$^b$ | 430$^{ab}$ |
| Feed intake (kg) | 16.3 | 27.5 | 18.8 |
| Feed conversion | 3.07 | 1.85 | 2.09 |

Notes:
The data are each the mean value per head for the 21-day period from infection to autopsy. Different alphabetic letters on the same line indicate that there is a significant difference between the data to which they are attached (P <0.05).
e.g. Significant difference between a and b; No significant difference between b and ab.

TEST EXAMPLE 6

Lankacidin C was tested at concentrations in feed of 100 ppm and lower by the same method as in Test Example 5, with carbadox, a commonly used anti-swine-dysentery agent, for comparison. The results obtained are summarized in Table 6. The feeding results also revealed that lankacidin C is a more excellent anti-swine-dysentery agent than carbadox.

TABLE 6

| Item examined | Group | | | | | |
|---|---|---|---|---|---|---|
| | Uninfected control (without drug) | Infected control | Lankacidin C | | | Carbadox |
| | | | 10 ppm | 50 ppm | 100 ppm | 50 ppm |
| Swine dysentery | | | | | | |
| Number of pigs showing signs of infection/number of pigs used | 0/4 | 4/4 | 0/4 | 0/4 | 0/4 | 0/4 |
| Number of days on which mucous bloody stool was observed (during the 21-day test period) | 0 | 9.5 | 0 | 0 | 0 | 0 |
| Number of days on which diarrhea was observed (during the 21-day test period) | 0.5 | 14.3 | 0 | 0 | 0 | 3.0 |
| Number of pigs from which the pathogen was detected | | | | | | |
| In feces | 0 | 4 | 0 | 0 | 0 | 0 |
| In colonic mucosa | 0 | 4 | 0 | 0 | 0 | 0 |
| Number of pigs showing colonic lesions | 0 | 4 | 0 | 0 | 0 | 0 |
| Feeding results | | | | | | |
| Body weight (kg) | | | | | | |
| At the time of infection | 11.1 | 10.2 | 10.5 | 11.1 | 11.1 | 11.1 |
| At the time of completion | 22.7$^a$ | 13.0$^b$ | 20.7$^a$ | 25.3$^a$ | 25.5$^a$ | 21.0$^a$ |
| Body weight gain (grams/day) | 551$^{abc}$ | 133$^d$ | 484$^{ac}$ | 673$^{ab}$ | 689$^b$ | 473$^c$ |
| Feed intake (kg) | 21.7 | 9.7 | 18.4 | 25.3 | 25.6 | 20.7 |
| Feed conversion | 1.87 | 3.45 | 1.81 | 1.79 | 1.77 | 2.08 |

Notes:
The data are each the mean value per head for the 21-day period from infection to autopsy. Different alphabetic letters on the same line indicate that there is a significant difference between the data to which they attached (P <0.05).
e.g. Significant difference between abc and d; No significant difference between abc and ac.

TEST EXAMPLE 7

The anti-swine-dysentery effects of 10 ppm each of lankacidin A and lankacidin C 14-propionate were examined by the procedure of Test Example 6. The results obtained are summarized in Table 7. Lankacidin A and lankacidin C 14-propionate both were distinctly effective against swine dysentery.

TABLE 7

| | Group | | | | |
|---|---|---|---|---|---|
| Item examined | Uninfected control (without drug) | Infected control | Lankacidin A 10 ppm | Lankacidin C 14-propionate 10 ppm | Carbadox 50 ppm |
| | Swine dysentery | | | | |
| Number of pigs showing signs of infection/number of pigs used | 0/4 | 4/4 | 0/4 | 0/4 | 0/4 |
| Number of days on which mucous bloody stool was observed (during the 21-day test period) | 0 | 11.3 | 0 | 0 | 0 |
| Number of days on which diarrhea was observed (during the 21-day test period) | 0 | 15.3 | 0 | 0 | 0 |
| Number of pigs from which the pathogen was detected | | | | | |
| In feces | 0 | 4 | 0 | 0 | 0 |
| In colonic mucosa | 0 | 4 | 0 | 0 | 0 |
| Number of pigs showing colonic lesions | 0 | 4 | 0 | 0 | 0 |
| | Feeding results | | | | |
| Body Weight (kg) | | | | | |
| At the time of infection | 10.7 | 10.8 | 11.0 | 11.4 | 11.1 |
| At the time of completion | 22.8 | 16.0 | 22.9 | 23.1 | 22.7 |
| Body weight gain (grams/day) | 576$^a$ | 248$^b$ | 567$^a$ | 562$^a$ | 552$^a$ |
| Feed intake (kg) | 21.2 | 12.7 | 21.0 | 21.1 | 21.2 |
| Feed conversion | 1.75 | 2.44 | 1.76 | 1.81 | 1.83 |

Notes:
The data are each the mean value per head for the 21-day period from infection to autopsy. Different alphabetic letters on the same line indicate that there is a significant difference between the data to which they are attached ($P < 0.05$).

TEST EXAMPLE 8

This test was conducted under the conditions of so-called therapeutic administration. Thus, the administration was begun immediately when pigs showed clinical signs of swine dysentery. The method of infection was the same as in Test Example 5. Five pigs were used which showed signs of the disease on the same day (6th day) after infection. Simultaneously with showing of the signs, the pigs were provided with a feed containing 50 ppm of lankacidin C. The results obtained are shown in Table 8. In all the cases, mucous bloody diarrhea was no more observed on the day following the administration but the passage was loose or normal. After 2 days, the viable count for the pathogen in feces was below the detection limit ($10^2$ CFU/g). Autopsy carried out 15 days after manifestation of the signs (9 days after discontinuation of administration) revealed no colonic lesions, without the pathogen being detected.

TABLE 8

| | pig No. | | | | |
|---|---|---|---|---|---|
| Days after manifestation of signs | 1 Condition of feces (No. of pathogen) | 2 Condition of feces (No. of pathogen) | 3 Condition of feces (No. of pathogen) | 4 Condition of feces (No. of pathogen) | 5 Condition of feces (No. of pathogen) |
| 0* | ◎ (8.0) | ◎ (6.0) | ◎ (7.1) | ◎ (6.8) | ◎ (7.1) |
| 1* | ◐ (4.3) | ○ (2.3) | ◐ (4.4) | ◐ (2.0) | ○ (2.0) |
| 2* | ○ (−) | ○ (−) | ○ (−) | ○ (−) | ○ (−) |
| 3* | ○ (−) | ○ (−) | ○ (−) | ○ (−) | ○ (−) |
| 4* | ○ (−) | ○ (−) | ○ (−) | ○ (−) | ○ (−) |
| 5* | ○ (−) | ○ (−) | ○ (−) | ○ (−) | ○ (−) |
| 6* | ○ (−) | ○ (−) | ○ (−) | ○ (−) | ○ (−) |
| 7 | ○ (−) | ○ (−) | ○ (−) | ○ (−) | ○ (−) |
| 8 | ○ (−) | ○ (−) | ○ (−) | ○ (−) | ○ (−) |
| 9 | ○ (−) | ○ (−) | ○ (−) | ○ (−) | ○ (−) |
| 10 | ○ (−) | ○ (−) | ○ (−) | ○ (−) | ○ (−) |
| 11 | ○ (−) | ○ (−) | ○ (−) | ○ (−) | ○ (−) |
| 12 | ○ (−) | ○ (−) | ○ (−) | ○ (−) | ○ (−) |
| 13 | ○ (−) | ○ (−) | ○ (−) | ○ (−) | ○ (−) |
| 14 | ○ (−) | ○ (−) | ○ (−) | ○ (−) | ○ (−) |
| 15 | ○ (−) | ○ (−) | ○ (−) | ○ (−) | ○ (−) |
| (Autopsy) colonic lesions | negative | negative | negative | negative | negative |
| No. of pathogen | (−) | (−) | (−) | (−) | (−) |

TABLE 8-continued

| | pig No. | | | | |
|---|---|---|---|---|---|
| | 1 | 2 | 3 | 4 | 5 |
| Days after manifestation of signs | Condition of feces (No. of pathogen) | Condition of feces (No. of pathogen) | Condition of feces (No. of pathogen) | Condition of feces (No. of pathogen) | Condition of feces (No. of pathogen) |
| in colon | | | | | |

Notes:
The condition of feces was rated at one of the following four classes: ○- normal; ◐ - loose; ◑- diarrheal; ⊙- mucous and bloody.
The viable count values are expressed in log/g; (−) indicates that the count is below the detection limit ($10^2$ CFU/g).
The symbol * indicates those days on which the feed containing 50 ppm of lankacidin C was given.

TEST EXAMPLE 9

Lankacidins were tested for therapeutic effects in swine dysentery under therapeutic conditions in the same manner as in Test Example 8. The effects were judged based on the condition of feces. The results obtained are shown in Table 9, indicating that lankacidin A, lankacidin C and lankacidin C 14-propionate are therapeutically effective at the dose level of 50 ppm.

TABLE 9

| Group Days after manifestation of signs | | Infected Control (without drug) | | | | Lankacidin A administered group (50 ppm) | | | | Lankacidin C administered group (50 ppm) | | | | Lankacidin C 14-propionate administered group (50 ppm) | | | |
|---|---|---|---|---|---|---|---|---|---|---|---|---|---|---|---|---|---|
| pig No. | | 1 | 2 | 3 | 4 | 5 | 6 | 7 | 8 | 9 | 10 | 11 | 12 | 13 | 14 | 15 | 16 |
| sex | | ♂ | ♂ | ♀ | ♀ | ♂ | ♂ | ♀ | ♀ | ♂ | ♂ | ♀ | ♀ | ♂ | ♂ | ♀ | ♀ |
| 0* | | ○ | ○ | ○ | ○ | ○ | ○ | ○ | ○ | ○ | ○ | ○ | ○ | ○ | ○ | ○ | ○ |
| 1* | | ○ | ○ | ○ | ○ | ◐ | ○ | ○ | ○ | ○ | ○ | ○ | ◐ | ◐ | ○ | ◐ | ○ |
| 2* | | ○ | ○ | ○ | ○ | ○ | ○ | ○ | ○ | ○ | ○ | ○ | ○ | ○ | ○ | ○ | ○ |
| 3* | | ○ | ○ | ○ | ○ | ○ | ○ | ○ | ○ | ○ | ○ | ○ | ○ | ○ | ○ | ○ | ○ |
| 4* | | ○ | ○ | ○ | ○ | ○ | ○ | ○ | ○ | ○ | ○ | ○ | ○ | ○ | ○ | ○ | ○ |
| 5* | | ○ | ○ | ○ | ○ | ○ | ○ | ○ | ○ | ○ | ○ | ○ | ○ | ○ | ○ | ○ | ○ |
| 6* | | ○ | ○ | ○ | ○ | ○ | ○ | ○ | ○ | ○ | ○ | ○ | ○ | ○ | ○ | ○ | ○ |
| 7 | | ○ | ○ | ○ | ○ | ○ | ○ | ○ | ○ | ○ | ○ | ○ | ○ | ○ | ○ | ○ | ○ |
| 8 | | ○ | ○ | ○ | ○ | ○ | ○ | ○ | ○ | ○ | ○ | ○ | ○ | ○ | ○ | ○ | ○ |
| 9 | | ○ | ○ | ○ | ○ | ○ | ○ | ○ | ○ | ○ | ○ | ○ | ○ | ○ | ○ | ○ | ○ |
| 10 | | ○ | ○ | ○ | ○ | ○ | ○ | ○ | ○ | ○ | ○ | ○ | ○ | ○ | ○ | ○ | ○ |
| 11 | | ○ | ○ | ○ | ○ | ○ | ○ | ○ | ○ | ○ | ○ | ○ | ○ | ○ | ○ | ○ | ○ |
| 12 | | ○ | ○ | ○ | ○ | ○ | ○ | ○ | ○ | ○ | ○ | ○ | ○ | ○ | ○ | ○ | ○ |
| 13 | | ◐ | ○ | ○ | ○ | ○ | ○ | ○ | ○ | ○ | ○ | ○ | ○ | ○ | ○ | ○ | ○ |
| 14 | | ◐ | ○ | ○ | ○ | ○ | ○ | ○ | ○ | ○ | ○ | ○ | ○ | ○ | ○ | ○ | ○ |
| 15 | | ◐ | ○ | ○ | ○ | ○ | ○ | ○ | ○ | ○ | ○ | ○ | ○ | ○ | ○ | ○ | ○ |
| 16 | | ◐ | ◑ | ○ | ○ | ○ | ○ | ○ | ○ | ○ | ○ | ○ | ○ | ○ | ○ | ○ | ○ |
| 17 | | ◐ | ◑ | ○ | ○ | ○ | ○ | ○ | ○ | ○ | ○ | ○ | ○ | ○ | ○ | ○ | ○ |
| 18 | | ◐ | ◑ | ○ | ○ | ○ | ○ | ○ | ○ | ○ | ○ | ○ | ○ | ○ | ○ | ○ | ○ |
| 19 | | ◐ | ◑ | ○ | ◑ | ○ | ○ | ○ | ○ | ○ | ○ | ○ | ○ | ○ | ○ | ○ | ○ |
| 20 | | ◐ | ◑ | ○ | ◑ | ○ | ○ | ○ | ○ | ○ | ○ | ○ | ○ | ○ | ○ | ○ | ○ |
| 21 | | ◐ | ◑ | ○ | ◑ | ○ | ○ | ○ | ○ | ○ | ○ | ○ | ○ | ○ | ○ | ○ | ○ |

Notes:
The condition of feces was rated at one of the following four classes; ○- normal; ◐- loose; ◑- diarrheal; ⊙ - mucous and bloody.
The symbol * indicates the days on which the feed containing 50 ppm of the drug was given.

As is evident from the results of the above Test Examples 1–9, compound (I) produces very excellent effects as an agent for preventing and treating swine dysentery, is superior to similar antibiotic anti-swine-dysentery agents already on the market, and therefore is very useful in livestock industry.

TEST EXAMPLE 10

Effects of compound (I) on the growth of pigs under the conditions in which swine dysentery was absent were examined. Thus, 40 one-month-old Landrace pigs (5 litters) were used in groups each consisting of 8 (4 males and 4 females). Lankacidin C was added in concentrations of 0 (control), 1, 2.5, 5 and 10 ppm to antibacterial agent-free starter feed for the period from the start of the test through the age of 3 months and to the feed for testing pigs for performance of meat production (also free of antibacterial agents) for the period from the age of 4 months to the age of 6 months (end). Thus, in each group, dietary lankacidin C was administered continuously for 5 months.

As the results summarized in Table 10 indicate, growth of pigs was increased in a manner almost proportional to the level of addition of lankacidin C, and accordingly the feed efficiency was improved. Thus, even under usual feeding conditions, compound (I) is useful for increasing swine meat production.

TABLE 10

| | Group | | | | |
|---|---|---|---|---|---|
| | Control | Lankacidin C | | | |
| Item examined | | 1 ppm | 2.5 ppm | 5 ppm | 10 ppm |
| Body weight (kg) | | | | | |
| At start | 7.4 | 7.4 | 7.4 | 7.4 | 7.4 |
| At feed exchange | $31.7^a$ | $32.7^a$ | $34.2^{ab}$ | $36.9^b$ | $37.5^b$ |
| At end | $101.4^a$ | $102.4^{ab}$ | $104.6^{ab}$ | $109.0^{ab}$ | $110.2^b$ |
| Body weight gain (kg) | | | | | |
| For starter feed period | $24.3^a$ | $25.4^{ab}$ | $26.9^b$ | $29.5^b$ | $30.1^b$ |
| For whole period | $94.0^a$ | $95.0^{ab}$ | $97.2^{ab}$ | $101.7^{ab}$ | $102.8^b$ |
| Feed intake (kg) | | | | | |
| For starter feed period | 49.9 | 49.4 | 49.1 | 50.7 | 51.2 |
| For whole period | 280.2 | 275.6 | 278.0 | 284.6 | 284.8 |
| Feed conversion | | | | | |
| For starter feed Period | 2.05 | 1.95 | 1.83 | 1.72 | 1.70 |

TABLE 10-continued

| | Group | | | | |
|---|---|---|---|---|---|
| | Con- | | Lankacidin C | | |
| Item examined | trol | 1 ppm | 2.5 ppm | 5 ppm | 10 ppm |
| For whole period | 2.98 | 2.90 | 2.86 | 2.80 | 2.77 |

Notes:
The data are each the mean value per head. Different alphabetic letters on the same line indicate that there is a significant difference between the data to which they are attached ($P < 0.05$).
e.g. Significant difference between a and b; no significant difference between ab and a or between ab and b.

TEST EXAMPLE 11

Fourty-eight 35-day-old Landrace pigs (6 litters) were used in 6 groups each consisting of 8 (4 males and 4 females). Lankacidin A was added in concentrations of 0 (control), 1, 2.5, 5, 10 and 20 ppm to antibacterial agent-free starter feed for the period from the start of the test through the age of 3 months and to the feed for testing pigs for performance of meat production (also free of antibacterial agents) for the period from the age of 4 months to the age of 6 months (end).

The growth data obtained in the 5-month continuous administration test are summarized in Table 11. Swine growth was promoted proportionally to the increase of level of addition of lankacidin A, and the feed efficiency was improved accordingly.

TABLE 11

| | Group | | | | | |
|---|---|---|---|---|---|---|
| | Control | Lankacidin A | | | | |
| Item examined | | 1 ppm | 2.5 ppm | 5 ppm | 10 ppm | 20 ppm |
| Body weight (kg) | | | | | | |
| At start | 9.19 | 9.18 | 9.16 | 9.16 | 9.15 | 9.18 |
| At feed exchange | 32.9$^a$ | 34.0$^{ab}$ | 34.6$^{ab}$ | 36.1$^{ab}$ | 36.7$^b$ | 37.4$^b$ |
| At end | 108.2$^a$ | 111.6$^{ab}$ | 113.5$^{ab}$ | 118.3$^{ab}$ | 120.5$^b$ | 123.4$^b$ |
| Body weight gain (kg) | | | | | | |
| For starter feed period | 23.7$^a$ | 24.8$^{ab}$ | 25.4$^{ab}$ | 26.9$^b$ | 27.6$^b$ | 28.8$^b$ |
| For whole period | 99.0$^a$ | 102.4$^{ab}$ | 104.4$^{ab}$ | 109.1$^{ab}$ | 111.4$^b$ | 114.2$^b$ |
| Feed intake (kg) | | | | | | |
| For starter feed period | 48.2 | 48.1 | 47.6 | 47.6 | 47.7 | 48.2 |
| For whole period | 290.1 | 294.9 | 295.3 | 304.3 | 305.2 | 310.6 |
| Feed conversion | | | | | | |
| For starter feed period | 2.03 | 1.94 | 1.87 | 1.77 | 1.73 | 1.71 |
| For whole period | 2.93 | 2.88 | 2.83 | 2.79 | 2.74 | 2.72 |

Notes:
The data are each the mean value per head. Different alphabetic letters on the same line indicate that there is a significant difference between the data to which they are attached ($P < 0.05$).

EXAMPLE 1

By incorporating compound (I) in the following basal feed or in a part of the materials therefor at an optional concentration, feeds for preventing or treating swine dysentery or for increasing swine productivity can be produced.

EXAMPLE 2

By incorporating compound (I) in the vitamin-mineral mixture shown as (a) or (b) hereinafter and basal feedstuff (e.g., defatted rice bran) together with amino acid (e.g., D,L-methionine, lysine hydrochloride) at an optional concentration, premixes of this invention can be produced.

| Composition of basal feed (%) | | |
|---|---|---|
| Materials | Starter milk | Feed for progeny test of meat production |
| Corn meal | 20.0 | 22.0 |
| Milo | | 22.0 |
| Barley flour | 19.0 | 22.0 |
| Wheat flour | 14.0 | |
| Soybean flour | 4.0 | |
| Wheat bran | 6.8 | 12.0 |
| Defatted rice bran | 4.0 | 4.0 |
| Fish meal | 3.0 | 4.0 |
| Soybean meal | 5.0 | 4.0 |
| Dried skim milk | 9.78 | |
| Dried whey | 5.0 | |
| Alfalfa meal | | 2.5 |
| Glucose | 5.0 | |
| Yeast for feed | 2.0 | |
| Powdered fat | 1.5 | |
| Calcium carbonate | | 1.5 |
| Sodium chloride | | 0.5 |
| Calcium triphosphate | 0.7 | 0.8 |
| Saccharine | 0.02 | |
| Vitamin-mineral mixture | 0.2$^a$ | 0.4$^b$ |
| DL-methionine | | 0.1 |
| Total | 100.0 | 100.0 |

$^a$Contains per kilogram: 2,500,000 IU of vitamin A, 500,000 IU of vitamin $D_3$, 0.75 g of vitamin E, 1 g of vitamin $B_1$.nitrate, 1.5 g of vitamin $B_2$, 0.25 g of vitamin $B_6$, 1 mg of vitamin $B_{12}$, 3.5 g of calcium pantothenate, 7.5 g of nicotinamide, 50 g of choline chloride, 50 g of iron, 5 g of cooper, 25 g of zinc, 15 g of manganese, 0.25 g of cobalt and 0.1 g of iodine.
$^b$The following mixtures A, B and C admixed in a ratio of 0.15:0.15:0.1 by weight were used.

Mixture A: 5% of manganese, 5% of iron, 1% of copper, 6% of zinc and 0.1% of iodine
Mixture B: 10,000 IU of vitamin A and 2000 IU of vitamin $D_3$ per gram
Mixture C: 1 g of vitamin $B_1$.nitrate, 7 g of vitamin $B_2$, 0.5 g of vitamin $B_6$, 6 g of nicotinamide, 10.9 g of calcium pantothenate and 57.6 g of choline hydrochloride per kilogram; supplemented with 10 μg of vitamin $B_{12}$.

What is claimed is:
1. A method for prophylaxis or treatment of swine dysentery or for increase of swine productivity, which comprises administering to swine, as an active ingredient, an effective amount of at least one compound of the formula:

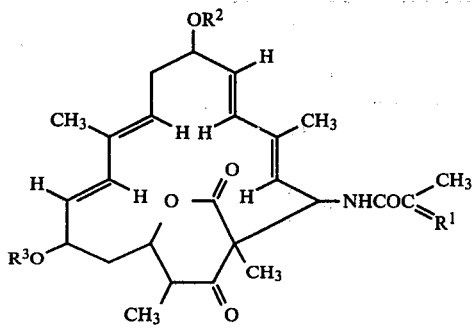

wherein $R^1$ is =O or

and $R^2$ and $R^3$ are each hydrogen, a $C_1$-$C_7$ fatty acid residue which is unsubstituted or substituted with phenyl on the terminal carbon atom thereof, benzoyl or nicotinoyl.

2. A method according to claim 1, wherein the active ingredient is orally administered at the dose level of about 0.025 to 25 mg per kilogram body weight daily.

3. A method according to claim 1, wherein a feed containing the active ingredient is orally administered ad libitum.

4. A method according to claim 3, wherein the feed containing the active ingredient in a weight concentration of about 1 to 500 ppm is administed for prophylaxis of swine susceptiple to swine dysentery.

5. A method according to claim 3, wherein the feed containing the active ingredient in a weight concentration of about 2 to 500 ppm is administered for treatment to swine infected with swine dysentery.

6. A method according to claim 3, wherein the feed containing the active ingredient in a weight concentration of about 0.5 to 200 ppm is administered for increase of swine productivity.

7. A method according to claim 1, wherein $R^1$ is =O, and $R^2$ and $R^3$ are each hydrogen or a $C_{1-7}$ fatty acid residue which is unsubstituted or substituted with phenyl on the terminal carbon atom thereof.

8. A method according to claim 7, wherein $R^2$ is hydrogen and $R^3$ is $C_{2-4}$ fatty acid residue which is unsubstituted or substituted with phenyl on the terminal carbon atom thereof.

9. A method according to claim 1, wherein the active ingredient is lankacidin A.

10. A method according to claim 1, wherein the active ingredient is a mixture of a predominant amount of lankacidin A with lankacidin C.

* * * * *